United States Patent [19]

Wagner et al.

[11] Patent Number: 6,030,767
[45] Date of Patent: Feb. 29, 2000

[54] INTRACELLULAR AND EXTRACELLULAR DECONTAMINATION OF WHOLE BLOOD AND BLOOD COMPONENTS BY AMPHIPHILIC PHENOTHIAZIN-5-IUM DYES PLUS LIGHT

[75] Inventors: Stephen J. Wagner, Columbia, Md.; Louis Cincotta, Andover, Mass.

[73] Assignees: The American National Red Cross, Falls Church, Va.; The Rowland Institute for Science, Cambridge, Mass.

[21] Appl. No.: 09/009,892

[22] Filed: Jan. 21, 1998

Related U.S. Application Data

[60] Provisional application No. 60/035,931, Jan. 21, 1997.

[51] Int. Cl.$^7$ .............................. A01N 1/02; C12N 7/06
[52] U.S. Cl. .............................................. 435/2; 435/238
[58] Field of Search ............................ 514/224.8; 435/2, 435/238

[56] References Cited

U.S. PATENT DOCUMENTS

| | | | |
|---|---|---|---|
| 4,181,128 | 1/1980 | Swartz | 128/207.21 |
| 4,305,390 | 12/1981 | Swartz | 128/207.21 |
| 4,402,318 | 9/1983 | Swartz | 604/20 |
| 4,407,282 | 10/1983 | Swartz | 604/20 |
| 4,585,735 | 4/1986 | Meryman et al. | 435/2 |
| 4,622,395 | 11/1986 | Bellus et al. | 544/37 |
| 4,775,625 | 10/1988 | Sieber | 435/238 |
| 4,878,891 | 11/1989 | Judy et al. | 604/5 |
| 4,962,197 | 10/1990 | Foley et al. | 544/31 |
| 5,220,009 | 6/1993 | Mazur et al. | 536/174 |
| 5,545,516 | 8/1996 | Wagner | 435/2 |
| 5,571,666 | 11/1996 | Floyd et al. | 435/2 |

FOREIGN PATENT DOCUMENTS

| | | |
|---|---|---|
| 0196 515 A1 | 10/1986 | European Pat. Off. . |
| 3305304A1 | 8/1984 | Germany . |
| WO 91/16911 | 11/1991 | WIPO . |
| WO 98/31219 | 7/1998 | WIPO . |

OTHER PUBLICATIONS

Lambrecht, B. et al., Vox Sang, vol. 60, p. 207–213, 1991.
Lambrecht, B. et al., Biologicals, vol. 22(3), p. 227–231, 1994.
The Merck Index, 11th ed., Merck & Co., Inc., p. 954, 1989.
Klein–Struckmeier, A. et al., Beitr Infusionsther Transfusionsmed. Basel, Karer, vol. 34, p. 43–47, 1997.
Mohr, H. et al., Photochem. & Photobiol., vol. 65(3), p. 441–445, 1997.
Wainwright, M. et al., FEMS Immunology & Medical Microbiology, vol. 19, p. 75–80, 1997.
Taylor et al., "Basic metachromatic cye, 1,9–dimethyl methylene blue", Histochem., J. 1 (3) : 199–204 (1969).
Wagner et al., "Factors Affecting Virus Photoinactivation by a Series of Phenothiazine Dyes", Photochemistry and Photobiology 67 (3):343–49 (1998).
Abe, H., and Wagner, S.J., "Analysis of Viral DNA, Protein and Envelope Damage after Methylene Blue, Phthalocyanine Derivative or Merocyanine 540 Photosensitization," Photochem. Photobiol. 61:402–409 (1995).
Cole, M., "Photochemical Inactivation of Virus in Red Cells," Transfusion 29:42S, Abstract No. S145 (Sep. 1989).
Floyd, R.A., et al., "Methylene Blue plus Light Mediates 8–Hyroxyguanine Formation in DNA," Arch. Biochem. Biophys. 273:106–111 (Aug. 1989).
Girotti, A.W., "Photosensitized Cross–Linking of Erythrocyte Membrane Proteins: Evidence Against Participation of Amino Groups in the Reaction," Biochim. Biophys. Acta 602:45–56–(1980).
Lagerberg, J.W.M., "Factors affecting the amount and the mode of merocyanine 540 binding to the membrane of the human erythrocytes. A comparison with the binding to leukemia cells," Biochim. Biophys. Acta 1235:428–436 (May 1995).
Simon, M.I., and Van Vanukis, H., "The Photodynamic Reaction of Methylene Blue with Deoxyribonucleic Acid," J. Mol. Biol. 4:488–499 (Jun. 1962).
Sass, M.D., et al.,"Evaluation of stored blood viability by methylene blue reduction," J. Lab. Clin. Med. 73:744–752 (May 1969).
Vyas, G.N., "Inactivation and removal of blood–borne viruses," Transfusion 35:367–70 (May 1995).
Wagner, S.J., et al. "Red blood cell alterations associated with virucidal methylene blue phototreatment," Transfusion 33:30–36 (Jan. 1993).

Primary Examiner—Sandra E. Saucier
Attorney, Agent, or Firm—Sterne, Kessler, Goldstein & Fox, P.L.L.C.

[57] ABSTRACT

This invention is directed to a method for inactivating pathogenic contaminants, such as viruses, bacteria, parasites and leukocytes, frequently found in whole blood or blood components, such as red blood cells or plasma, which comprises treating whole blood or blood components with an amphiphilic phenothiazin-5-ium dye and light. Preferred amphiphilic phenothiazin-5-ium dyes are those having the formula

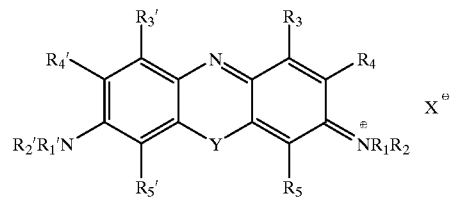

wherein each of $R_1$, $R_1'$, $R_2$, and $R_2'$ is independently selected from the group consisting of an alkyl group, an alkenyl group, an alkynyl group, a nitrile, an aralkyl group, a hydroxy group, an alkoxy group, an amine group, and a hydrogen atom, each of $R_3$, $R_3'$, $R_4$, $R_4'$, $R_5$ and $R_5'$ is independently selected from the group consisting of an alkyl group, an alkenyl group, an alkynyl group, a nitrile, an azide, an aryl group, an aralkyl group, a heteroaryl group, a hydroxy group, an alkoxy group, an aryloxy group, an amine group, and a hydrogen atom, or any two of $R_1$, $R_1'$, $R_2$, $R_2'$, $R_3$, $R_3'$, $R_4$, $R_4'$, $R_5$ and $R_5'$ together form a aryl or heteroaryl ring; Y is selected from the group consisting of S, Se and Te; and X is a counter-ion.

19 Claims, 7 Drawing Sheets

1 - NT, DAY 0
2 - 4-91, DAY 1
3 - 4-91, DAY 21
4 - NT, DAY 21

INTRACELLULAR AND EXTRACELLULAR DECONTAMINATION OF WHOLE BLOOD AND BLOOD COMPONENTS BY AMPHIPHILIC PHENOTHIAZIN-5-IUM DYES PLUS LIGHT

This application claims the benefit of the filing date of U.S. Provisional Application Ser. No. 60/035,931.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government therefore has certain rights in this invention.

FIELD OF THE INVENTION

This invention is directed to methods for reducing the level of active pathogenic contaminants, such as viruses, bacteria and parasites, frequently found in whole blood and blood components, including red blood cells, platelets and plasma.

BACKGROUND OF THE INVENTION

Among the risks inherent in handling or being transfused with blood, blood proteins, or other blood components is the risk of infection from pathogenic contaminants, including human immunodeficiency virus (HIV), serum hepatitis, cytomegalovirus, Epstein-Barr virus, herpes simplex, infectious mononucleosis, syphilis and malaria. Virucidal methods, including heat, solvent-detergent, and gamma irradiation, have been used to produce non-infectious plasma derivatives, but such methods are generally ineffective or too harsh to be routinely used for effective decontamination of whole blood, red cells and/or platelets. Indeed, any virucidal treatment that damages or introduces harmful or undesirable contaminants into the product is unsuitable for decontamination of a product intended for transfusion into an animal, particularly a human. Because of the critical need for transfusible red blood cells, it is of great importance to develop methods that can be readily used to decontaminate cellular blood components and whole blood without substantially or irreversibly altering or harming them.

Decontamination treatments that inactivate contaminating pathogens but do not harm the cellular fractions of blood are not readily available. Common decontamination treatments include the use of photosensitizers, which, in the presence of oxygen and upon exposure to light that includes wavelengths absorbed by the photosensitizer, inactivate viruses (EP 0 196 515). Typically, such photochemicals are dyes or other compounds that readily absorb UV or visible light in the presence of oxygen. These compounds include merocyanine 540 ("MC 540") (U.S. Pat. No. 4,775,625) and porphyrin derivatives (U.S. Pat. No. 4,878,891), as well as other photosensitizers.

Increased virucidal activity of these compounds is realized when the absorption spectrum of the photosensitizer does not significantly overlap the absorption spectra of pigments present in the blood, such as hemoglobin. In order to minimize cellular damage, it is preferable that the photosensitizer be nontoxic to cellular blood components and selectively bind to a component of the virus either that is not present in red cells or platelets or, if present therein, that is not essential to red cells' or platelets' function. It is also preferable if the photodynamic treatment inactivates both extracellular and intracellular viruses as well as proviruses. It is further preferable that the virucidal activity of the photosensitizer be uninhibited by the presence of plasma proteins, such as coagulation proteins, albumin and the like.

Treatment with known photochemicals, however, frequently does damage cellular blood components. For example, photochemicals such as the porphyrins (U.S. Pat. No. 4,878,891) and MC 540 (U.S. Pat. No. 4,775,625) cause membrane damage in the presence of light and oxygen, which significantly reduces the survivability of the phototreated red cells during storage. Similarly, treatment of red blood cells using phthalocyanine 4 with type 1/type 2 quenchers caused red cell damage even under optimized conditions—about 2% of the cells hemolyze after 21 days of storage (the current FDA guideline for hemolysis is ≦1% after 6 weeks of storage at 1–6° C.) (*Transfusion* 35:367–70 (1995)).

Additionally, both MC 540 and porphyrin derivatives apparently bind to blood components, such as albumin (*Transfusion* 29:42S (1989); *Biochim. Biophys. Acta* 1235:428–436 (1995)). For example, the effect of MC 540 on platelets and the influence of albumin on MC 540's virucidal activity has been studied. Platelets exhibited a MC 540 dose-dependent decrease in response to thrombin in the absence of light. In the presence of light and MC 540, the platelets aggregated. Albumin, however, prevented aggregation and inhibited the inactivation of viral contaminants by MC 540 plus light. Similarly, because of such competitive inhibition reactions with blood and/or plasma components, other dyes are not suitable for decontaminating blood, cellular blood components, or any blood-derived products containing high plasma concentrations (as plasma concentration increases, the percentage of viral inactivation substantially decreases).

Charged phenothiazin-5-ium dyes such as methylene blue, toluidine blue O, thionine, azure A, azure B, and azure C have been shown to inactivate animal viruses (U.S. Pat. Nos. 4,407,282, 4,402,318, 4,305,390, and 4,181,128). One target for virus inactivation is viral nucleic acids (Abe et al., *Photochem. Photobiol.* 61:402–409 (1995)). Methylene blue and visible light damage guanine residues of nucleic acids (Simon et al., *J Mol. Biol.* 4:488–499 (1962)). Methylene blue and white light produce 8-hydroxy-guanine in DNA (Floyd et al., *Arch. Biochim. Biophys.* 273:106–111 (1989)). Based on this activity, these dyes have been employed for inactivation of extracellular enveloped viruses in blood and blood components (U.S. Pat. No. 5,545,516).

These particular phenothiazin-5-ium dyes, however, have certain drawbacks that limit their usefulness for inactivating pathogens in whole blood or blood components. For example, red cells readily take up or bind such dyes (Sass et al., *J. Lab. Clin. Med* 73:744–752 (1969)). In addition, photosensitized oxidation of biological membranes is deleterious to membrane structure and function (methylene blue cross-links the membrane protein, spectrin, in erythrocytes exposed to visible light and oxygen) (Girotti, *Biochim. Biophys. Acta.* 602:45–56 (1980)). Also, methylene blue treated red blood cells have been shown to bind to plasma proteins, such as IgG and albumin (Wagner et al., *Transfusion* 33:30–36 (1992)). Finally, because of their hydrophilic character, these dyes cannot readily cross the cell membrane of cellular blood components and so are less effective at reducing the intracellular level of active pathogenic contaminants.

No method has therefore proven fully successful for decontaminating whole blood, blood components, or compositions containing concentrated blood components, including high levels of plasma. There remains, however, an acute need for a safe and effective method for reducing the level of active pathogenic contaminants, particularly HIV and hepatitis, in whole blood or blood components without rendering the blood or blood components unsuitable for transfusion.

Additionally, any method employed to decontaminate blood should not adversely affect the survivability of red blood cells during prolonged storage. During storage, human red blood cells undergo morphological and biochemical changes, including: decreases in the intracellular levels of adenosine triphosphate ("ATP")(associated with the fluidity of the cellular membrane, which is essential for the passage of cells through the narrow channels in the spleen and liver), 2,3 diphosphoglycerate ("2,3-DPG") (which is associated with the ability of the hemoglobin in the red cells to deliver oxygen to the tissues), and potassium (which is associated with, inter alia, transport of ions across the cell membrane); changes in cellular morphology, such as spicule formation (which reduces the surface area of the cell and, as a consequence, the ability of the cell to deform on passing through narrow channels); and progressive hemolysis (which causes an overall reduction in the number of viable cells for transfusion). These changes can be monitored to observe the effects of decontamination methods on the survivability of the red blood cells and their suitability for transfusion.

Solutions that prolong the shelf life of red cells are known (U.S. Pat. No. 4,585,735). Typically, such solutions contain citrate, phosphate, glucose, adenine, and other ingredients and function to prolong shelf life by maintaining the levels of ATP and 2,3-DPG in the cells. Solutions that contain a membrane-penetrating salt, such as ammonium acetate, in addition to phosphate, glucose, and adenine, and that are hypotonic with respect to molecules that are unable to penetrate the cell membrane have been shown to maintain the levels of ATP for more than 100 days of refrigeration (U.S. Pat. No. 4,585,735).

SUMMARY OF THE INVENTION

Accordingly, it is an object of the present invention to provide methods of reducing the level of active pathogenic contaminants, both intracellular and extracellular, in whole blood and blood components, including cellular blood components and liquid blood components, without rendering them unsuitable for transfusion. Other objects, features and advantages of the present invention will be set forth in the detailed description of preferred embodiments that follows, and in part will be apparent from the description or may be learned by practice of the invention. These objects and advantages of the invention will be realized and attained by the compositions and methods particularly pointed out in the written description and claims hereof.

In accordance with these and other objects, a first embodiment of the present invention is directed to a method for decontaminating whole blood and/or blood components, comprising the steps of: (a) adding an effective amount of at least one amphiphilic phenothiazin-5-ium dye to whole blood or blood components; and (b) irradiating the amphiphilic phenothiazin-5-ium dye-containing whole blood or blood components for a time sufficient to reduce the level of active pathogenic contaminants therein. In preferred embodiments of the present invention, the blood components are cellular blood components, such as red blood cells (RBCs) and platelets, liquid blood components, such as plasma, or mixtures of cellular and/or liquid blood components.

A second embodiment of the present invention is directed to certain amphiphilic phenothiazin-5-ium dyes which are particularly useful in the methods of the present invention and have the formula wherein X, Y, $R_1$, $R_1'$, $R_2$, $R_2'$, $R_3$, $R_3'$, $R_4$, $R_4'$, $R_5$ and $R_5'$ are defined below.

It is to be understood that both the foregoing general description and the following detailed description are exemplary and explanatory only and are intended to provide further explanation of the invention as claimed.

DETAILED DESCRIPTION OF THE PREFERRED EMBODIMENTS

Definitions

Unless defined otherwise, all technical and scientific terms used herein are intended to have the same meaning as is commonly understood by one of ordinary skill in the relevant art. All patents and publications mentioned herein are expressly incorporated by reference.

As used herein, the term "pathogenic contaminant of whole blood or blood components" is intended to mean a contaminant that, upon handling or transfusion into a recipient may cause disease in the handler and/or recipient. Examples of such pathogenic contaminants include, but are not limited to, the following: viruses, such as retroviruses (e.g. HIV) and hepatitis viruses; bacteria, such as E. coli; parasites, such as Trypanosoma; and leukocytes, such as lymphocytes (which can be a reservoir for harboring intracellular viruses).

As used herein, the term "blood components" is intended to mean one or more of the components that may be separated from whole blood and include, but are not limited to, cellular blood components, such as red blood cells and platelets; blood proteins, such as blood clotting factors, enzymes, albumin, plasminogen, and immunoglobulins; and liquid blood components, such as plasma and plasma-containing composition.

As used herein, the term "cellular blood component" is intended to mean one or more of the components of whole blood that comprises cells, such as red blood cells or platelets.

As used herein, the term "blood protein" is intended to mean one or more of the proteins that are normally found in whole blood. Illustrative examples of blood proteins found in mammals (including humans) include, but are not limited to, coagulation proteins (both vitamin K-dependent, such as Factor VII or Factor IX, and non-vitamin K-dependent, such as Factor VIII and von Willebrands factor), albumin, lipoproteins (high density lipoproteins and/or low density lipoproteins), complement proteins, globulins (such as immunoglobulins IgA, IgM, IgG and IgE), and the like.

As used herein, the term "liquid blood component" is intended to mean one or more of the fluid, non-cellular components of whole blood, such as plasma (the fluid, non-cellular portion of the blood of humans or animals as found prior to coagulation) or serum (the fluid, non-cellular portion of the blood of humans or animals after coagulation).

As used herein, the term "composition containing a cellular blood component and/or a blood protein" is intended to mean a composition that contains a biologically compatible solution, such as ARC-8, and one or more cellular blood components, one or more blood proteins, or a mixture of one or more cellular blood components and/or one or more blood proteins. Such compositions may also contain a liquid blood component, such as plasma.

Compositions containing a cellular blood component and/or a blood protein may optionally be leukodepleted. As used herein, the term "leukodepleted" is intended to mean that the concentration of leukocytes in the composition has been reduced by a specified amount, such as a factor of $10^5$. It is not necessary that compositions be leukodepleted before application of the methods of the present invention.

As used herein, a "transfusible composition" is intended to mean a composition that can be transfused into the blood stream of a mammal. Transfusible compositions may contain whole blood, one or more blood components, such as one or more cellular blood components, one or more blood proteins, and one or more liquid blood components, or mixtures of whole blood and one or more blood components, such as red blood cells, clotting factors or plasma.

As used herein, "decontamination" is intended to mean a process whereby the level of active pathogens, such as viral or bacterial contaminants, in a given composition is reduced. Such reduction may occur by rendering the pathogens inactive and/or noninfectious or by reducing the number of pathogens in the composition. A composition containing whole blood or a blood component that has been "decontaminated" can be transfused or manipulated without harming or infecting anyone exposed thereto.

As used herein, the term "pathogen" is intended to mean any replicable agent that may be found in or infect whole blood or blood components. Such pathogens include the various viruses, bacteria, parasites, and leukocytes known to those of skill in the art to generally be found in or infect whole blood or blood components. Illustrative examples of such pathogens include, but are not limited to: bacteria, such as Streptococcus species, Escherichia species, and Bacillus species; viruses, such as human immunodeficiency viruses and other retroviruses, herpes viruses, paramyxoviruses, cytomegaloviruses, hepatitis viruses (including hepatitis B and hepatitis C), pox viruses, and toga viruses; parasites, such as malarial parasites, including Plasmodium species, and trypanosomal parasites; and leukocytes, such as lymphocytes.

The ratio of the titer of the control sample to the titer of virus in each of the treated samples is a measure of viral inactivation. As used herein, the term "$\log_{10}$, inactivation" is intended to mean the $\log_{10}$ of this ratio. Typically, a $\log_{10}$ inactivation of at least about 4 indicates that the treated sample has been decontaminated.

As used herein, the term "fluence" is intended to mean a measure of the energy per unit area of sample and is typically measured in joules/cm$^2$ (J/cm$^2$). As used herein, the term "fluence rate" is intended to mean a measure of the amount of energy that strikes a given area of a sample in a given period of time and is typically measured as milliwatts (mW)/cm$^2$ or as joules/cm$^2$ per unit time of exposure.

As used herein, the term "amphiphilic phenothiazin-5-ium dye" is intended to mean a compound having the general structure which is soluble in aqueous solutions and also capable of passing through the cell membrane of red blood cells in sufficient amounts to reduce the level of active intracellular pathogenic contaminants upon irradiation with light of a suitable intensity and wavelength.

The unspecified valences of the carbon and nitrogen atoms in the formula above may be occupied by hydrogen atoms or by any organic or inorganic moiety which does not adversely affect the amphiphilic character of the dye. While not wishing to be bound by any theory of operability, it is believed that the selection of a particular substituent group or combination of groups on the phenothiazin-5-ium ring skeleton affects the amphiphilic character of such charged dyes. One skilled in the art may determine the suitability of a particular substituent group or groups empirically using any of the standard assays for determining the level of active intracellular pathogenic contaminants.

Illustrative examples of organic moieties include, but are not limited to, alkyl groups, alkenyl groups, alkynyl groups, hydroxy groups, alkoxy groups, aryl groups, heteroaryl groups, aryloxy groups, heteroaryloxy groups, nitro groups, amine groups, amide groups, alkylcarboxyl groups, arylcarboxyl groups, aralkyl groups, cyano groups, azide groups, haloalkyl groups, haloaryl groups. Preferable organic moieties include alkyl groups, such as methyl, ethyl, and propyl, alkenyl groups, such as ethenyl, alkynyl groups, such as acetenyl, and amine groups, such as monomethylamine and dimethylamine.

Illustrative examples of suitable inorganic moieties include, but are not limited to, sulfur, selenium and tellurium. Preferred inorganic moieties include sulfur and selenium.

As used herein, the term "leukocyte depleted blood component" is intended to mean a blood component, such as plasma, as defined above that has been filtered through a filter that depletes the concentration of leukocytes in the plasma by a factor of at least $10^2$. Such filters are identified by the log of the factor by which the blood component is depleted of leukocytes.

As used herein, the term "extracellular pH" is intended to mean the pH of the liquid medium in which cellular blood components, such as red blood cells, are stored or maintained.

As used herein, the term "a biologically compatible solution" is intended to mean an aqueous solution which cellular blood components may be exposed, such as by being suspended therein, and remain viable, i.e., retain their essential biological and physiological characteristics. Such biologically compatible solutions preferable contain an effective amount of at least one anticoagulant.

As used herein, the term "a biologically compatible buffered solution" is intended to mean a biologically compatible solution having a pH and osmotic properties (e.g, tonicity, osmolality and/or oncotic pressure) suitable for maintaining the integrity of the cell membrane of cellular blood components. Suitable biologically compatible buffered solutions typically have a pH between 5 and 8.5 and are isotonic or only moderately hypotonic or hypertonic. Biologically compatible buffered solutions are known and readily available to those of skill in the art. Illustrative examples of suitable solutions include, but are not limited to, those listed in Table I below.

TABLE I

Common Biologically Compatible Buffered Solutions

| Ingredient | CPDA-1* (mM) | Unisol (mM) | Arc 8 (mM) |
| --- | --- | --- | --- |
| sodium citrate | 89.6 | 17.3 | 33.3 |
| citric acid | 15.6 | 2.7 | — |
| glucose | — | — | 139 |
| dextrose | 161.0 | 35.5 | — |
| NaH$_2$PO$_4$ | 16.1 | — | 2.9 |
| Na$_2$HPO$_4$ | — | 3.0 | 12.0 |
| Adenine | 2.0 | 2.2 | 2.0 |
| Mannitol | — | — | — |
| NaCl | — | 110.4 | — |
| KCl | — | 5.1 | — |
| CaCl$_2$ | — | 1.7 | — |
| MgCl$_2$ | — | 4.0 | — |
| NaHCO$_3$ | — | 40.0 | — |
| pH | 5.7 | 7.4 | 7.4 |

*CPDA- 1 is sold by Baxter Travenol.

Preferred Embodiments

As a first step when practicing any of the embodiments of the invention disclosed herein, whole blood is preferably drawn from a donor into a suitable biologically compatible buffered solution containing an effective amount of at least one anticoagulant. Suitable anticoagulants are known to those skilled in the art, and include, but are not limited to, lithium, potassium or sodium oxalate (15 to 25 mg/10 mL blood), sodium citrate (40 to 60 mg/10 mL blood), heparin sodium (2 mg/10 mL blood), disodium EDTA (10 to 30 mg/10 mL whole blood) or ACD-Formula B solution (1.0 mL/10 mL blood).

The whole blood so collected may then be decontaminated according to the methods of the present invention. Alternatively, the whole blood may first be separated into blood components, including, but not limited to, plasma, platelets and red blood cells, by any method known to those of skill in the art.

For example, blood can be centrifuged for a sufficient time and at a sufficient centrifugal force to sediment the red blood cells. Leukocytes collect primarily at the interface of the red cells and the plasma-containing supernatant in the buffy coat region. The supernatant, which contains plasma, platelets, and other blood components, may then be removed and centrifuged at a higher centrifugal force, whereby the platelets sediment.

Human blood normally contains about $7 \times 10^9$ leukocytes per liter. The concentration of leukocytes, which pellet with the red cells, can be decreased if desired by filtering through a filter that decreases their concentration by selected orders of magnitude. Leukocytes can also be removed from each of the components by filtration through an appropriate filter that removes them from the solution.

In a preferred embodiment of this invention, the whole blood or blood component to be decontaminated is obtained in, prepared in or introduced into gas permeable blood preservation bags, which are sealed and flattened to a width sufficiently narrow to permit light to irradiate the contents, such that any pathogenic contaminant present in the blood or blood component in the bag will be irradiated. Any such blood bag known to those of skill in the art may be used provided that the bag is transparent to the selected wavelength of light.

In a more preferred embodiment of this invention, the gas permeable blood preservation bag also contains oxygen. While not wishing to be bound by any theory of operability, it is believed that certain species of amphiphilic phenothiazin-5-ium dyes employed in the methods of the invention, in addition to intercalating between base pairs of DNA, generate singlet oxygen when irradiated with light of an appropriate wavelength. As is known to those skilled in the art, singlet oxygen directly or products thereof cause viral inactivation. Accordingly, it is preferred that, at least for certain species of amphiphilic phenothiazin-5-ium dyes, the composition being decontaminated contain a suitable amount of oxygen.

The composition that is to be decontaminated may also include any suitable biologically compatible buffer known to those of skill in the art. Examples of such buffers include, but are not limited to, Unisol and ARC 8.

The preferred amphiphilic phenothiazin-5-ium dyes employed in the methods of the present invention include those of the formula:

wherein
- each of $R_1$, $R_1'$, $R_2$, and $R_2'$ is independently selected from the group consisting of an alkyl group, an alkenyl group, an alkynyl group, a nitrile, an aralkyl group, a hydroxy group, an alkoxy group, an amine group, and a hydrogen atom,
- each of $R_3$, $R_3'$, $R_4$, $R_4'$, $R_5$ and $R_5'$ is independently selected from the group consisting of an alkyl group, an alkenyl group, an alkynyl group, a nitrile, an azide, an aryl group, an aralkyl group, a heteroaryl group, a hydroxy group, an alkoxy group, an aryloxy group, an amine group, and a hydrogen atom, or
- any two of $R_1$, $R_1'$, $R_2$, $R_2'$, $R_3$, $R_3'$, $R_4$, $R_4'$, $R_5$ and $R_5'$ together form a aryl or heteroaryl ring; Y is selected from the group consisting of S, Se and Te; and
- X is a counter-ion; with the provisos:
  (i) that if each of $R_1$, $R_1'$, $R_2$ and $R_2'$ is independently a hydrogen atom or an alkyl group, then at least one of $R_3$, $R_3'$, $R_4$, $R_4'$, $R_5$ and $R_5'$ is other than a hydrogen atom,
  (ii) that if one of $R_4$ and $R_4'$ is an alkyl group, then at least one other of $R_3$, $R_3'$, $R_4$, $R_4'$, $R_5$ and $R_5'$ is other than a hydrogen atom,
  (iii) that if any two of $R_3$, $R_3'$, $R_4$, $R_4'$, $R_5$ and $R_5'$ together form a fused aryl or heteroaryl ring, each of $R_1$, $R_1'$, $R_2$, $R_2'$ is other than a hydrogen atom.

As used herein, the term "alkyl group" is intended to mean a straight or branched chain hydrocarbon radical having from 1 to 10 carbon atoms, preferably 1 to 5 carbon atoms, and more preferably 1 or 2 carbon atoms, such as methyl, ethyl and the like.

As used herein, the term "alkenyl group" is intended to mean a straight or branched chain hydrocarbon radical having from 2–10 carbon atoms and at least one double bond, such as ethenyl or propenyl and the like.

As used herein, the term "alkynyl group" is intended to mean a straight or branched chain hydrocarbon radical having from 2–10 carbon atoms and at least one triple bond, such as ethynyl or propynyl and the like.

As used herein, the term "aryl group" is intended to mean a monocyclic or bicyclic aromatic hydrocarbon radical having from 6–12 carbon atoms in the ring(s), such as phenyl or naphthyl and the like.

As used herein, the term "aralkyl group" is intended to mean a straight or branched chain hydrocarbon radical having from 1 to 6 carbon atoms bound to a monocyclic or bicyclic aromatic hydrocarbon radical having from 6–12 carbon atoms in the ring(s), such as benzyl or 2-phenylethyl and the like.

As used herein, the term "heteroaryl group" is intended to mean a monocyclic or bicyclic aromatic radical having from 4–11 carbon atoms and at least one heteroatom (i. e. an oxygen atom, a nitrogen atom and/or a sulfur atom) in the ring(s), such as thienyl, furyl, pyranyl, pyridyl, quinolyl and the like.

In a preferred embodiment of the present invention, each of $R_1$, $R_1'$, $R_2$ and $R_2'$ is independently a methyl group, an ethyl group or a hydrogen atom. In a more preferred embodiment, each of $R_1$, $R_1'$, $R_2$, $R_2'$, $R_3$ and $R_3'$ is a methyl group.

In another preferred embodiment of the present invention, each of $R_3$ and $R_3'$ is independently an alkyl group.

In yet another preferred embodiment of the present invention, each of $R_1$, $R_1'$, $R_2$, and $R_2'$, is independently a lower alkyl group (i e. an alkyl group having 1–6 carbon atoms), a lower alkynyl group, or a hydrogen atom, and each of $R_3$, $R_3'$, $R_4$, $R_4'$, $R_5$ and $R_5'$ is independently a lower alkyl group, a lower alkynyl group, or a hydrogen atom. More preferably, the lower alkyl group is a methyl group or an ethyl group.

Preferably, Y is a sulfur atom or a selenium atom. More preferably, Y is a sulfur atom.

The counter ion X may be any anion, monovalent or polyvalent, sufficient to balance the charge on the amphiphilic phenothiazin-5-ium dye. Illustrative examples of suitable counter ions include inorganic moieties, such as halides (preferably chloride or bromide), sulfates and phosphates, and organic moieties, such as acetate, citrate and tartrate.

The amphiphilic phenothiazin-5-ium dyes used in the methods of the present invention may be prepared according to the methods and techniques known to those skilled in the art. Suitable synthetic methods are described, for example, in U.S. Pat. No. 4,962,197.

An effective amount of at least one selected dye is introduced into the composition. As used herein, the term "effective amount" is intended to mean an amount sufficient to provide a concentration of dye in the composition that is acceptable for transfusion and which is effective to reduce the level of active pathogens in the composition when irradiated with light of an appropriate intensity and wavelength. Preferably, the selected dye is non-toxic and the effective concentration is acceptable for transfusion so that the treated blood or blood component does not require additional manipulation to remove the dye and thereby risk contamination.

The effective concentration of dye to be used can be determined empirically by one of skill in the art. Preferably, the effective concentration of the dye is about 0.2 $\mu$M to about 50 $\mu$M, more preferably about 1 $\mu$M to about 25 $\mu$M.

In a particularly preferred embodiment of the present invention, 1,9-dimethyl methylene blue is employed as the amphiphilic phenothiazin-5-ium dye. Preferably, the 1,9-dimethyl methylene blue is introduced into the whole blood or blood component to be decontaminated at a concentration of about 1 $\mu$M to about 25 $\mu$M.

The mixture of the whole blood and/or blood component and amphiphilic phenothiazin-5-ium dye is then irradiated with light of an appropriate wavelength (or mixture of wavelengths) and intensity. As used herein, the term "appropriate wavelength and intensity" is intended to mean light of a wavelength and intensity that can be absorbed by the dye, but does not damage the blood or blood components present. It is well within the level of skill in the art to select such wavelength and intensity empirically based on certain relevant parameters, such as the particular dye employed and its concentration in the composition. For example, one having skill in the art would know that if the intensity of the light source is decreased, a greater concentration of dye and/or longer exposure time should probably be used.

An appropriate wavelength is preferably selected based on the absorption profile of the dye (or dyes) employed and is most preferably one that does not result in substantial damage to one or more of the cellular blood components in the composition being decontaminated.

Model viral systems are known to those of skill in the art which may be used to test the selected dye and light source for their efficacy. Such model viral systems include, but are not limited to, the enveloped bacteriophage Φ6, vesicular stomatitis virus (an animal virus that contains its genome encoded in DNA), and Sindbis virus (an animal virus that contains its genome encoded as RNA). Based on the effective values of parameters such as wavelength and light intensity measured for such model systems, one of skill in the art can routinely select suitable values for these parameters for use in practice of the present invention.

In a preferred embodiment of this invention, red blood cells, which have optionally been leukodepleted with a five log filter, are first suspended in ARC 8 at a hematocrit of about 15 to 55%, then introduced into gas permeable blood preservation bags in an amount such that the filled bag has a thickness of about 4 mm, and finally treated with 1,9-dimethyl methylene blue at a concentration of about 1 $\mu$M up to about 25 $\mu$M. This mixture is then irradiated with red light of wavelength 560 to 800 nm at a sufficient intensity for a sufficient time, such as 3.6 joule/cm$^2$ for about 60 minutes, to reduce the level of active pathogenic contaminants in the red blood cells and ARC 8 solution.

In other embodiments of this invention, compositions containing platelets and compositions containing high concentrations of plasma may be decontaminated by exposure for a sufficient time to an effective amount of an amphiphilic phenothiazin-5-ium dye plus an light of an appropriate wavelength and intensity.

Following treatment in accordance with the method of this invention, the whole blood, blood components or composition containing one or more of these may be stored or transfused. Alternatively, after treatment of compositions such as red cell preparations or platelet-rich plasma, the composition can be centrifuged at a force sufficient to pellet the cellular components. The supernatant can be removed following centrifugation and the cells resuspended to reduce the concentration of residual photosensitizer and any reaction products.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

EXAMPLE 1

Figure 1:
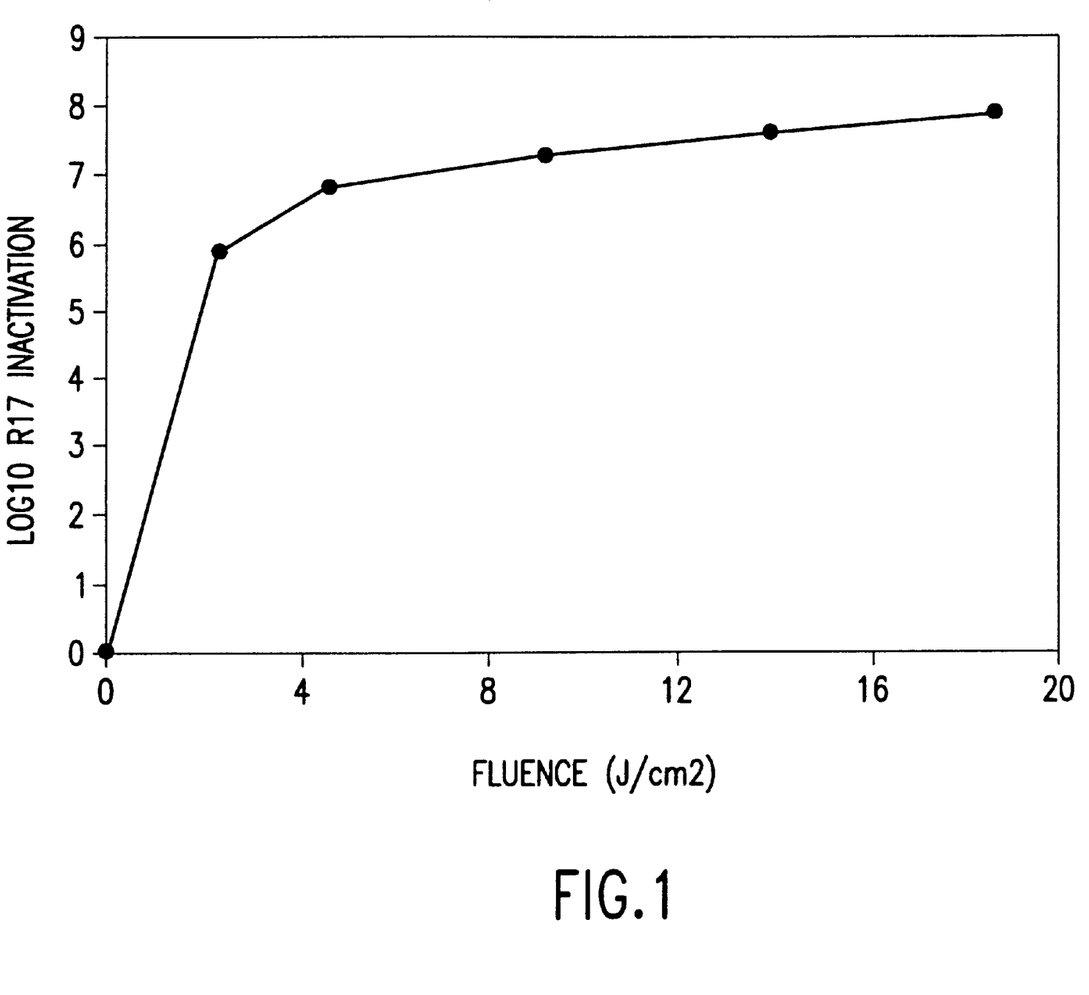
FIG. 1. Inactivation of R17 by Compound 4-91 and Light. Data from Example 1 are graphed here and show the effects of light intensity on the photoinactivation of the non-enveloped, single-stranded RNA bacteriophage R17 in plasma containing red cells (30% hematocrit) suspended in ARC-8 using 4 μM of 1,9-dimethyl methylene blue (compound 4-91).
Figure 5:
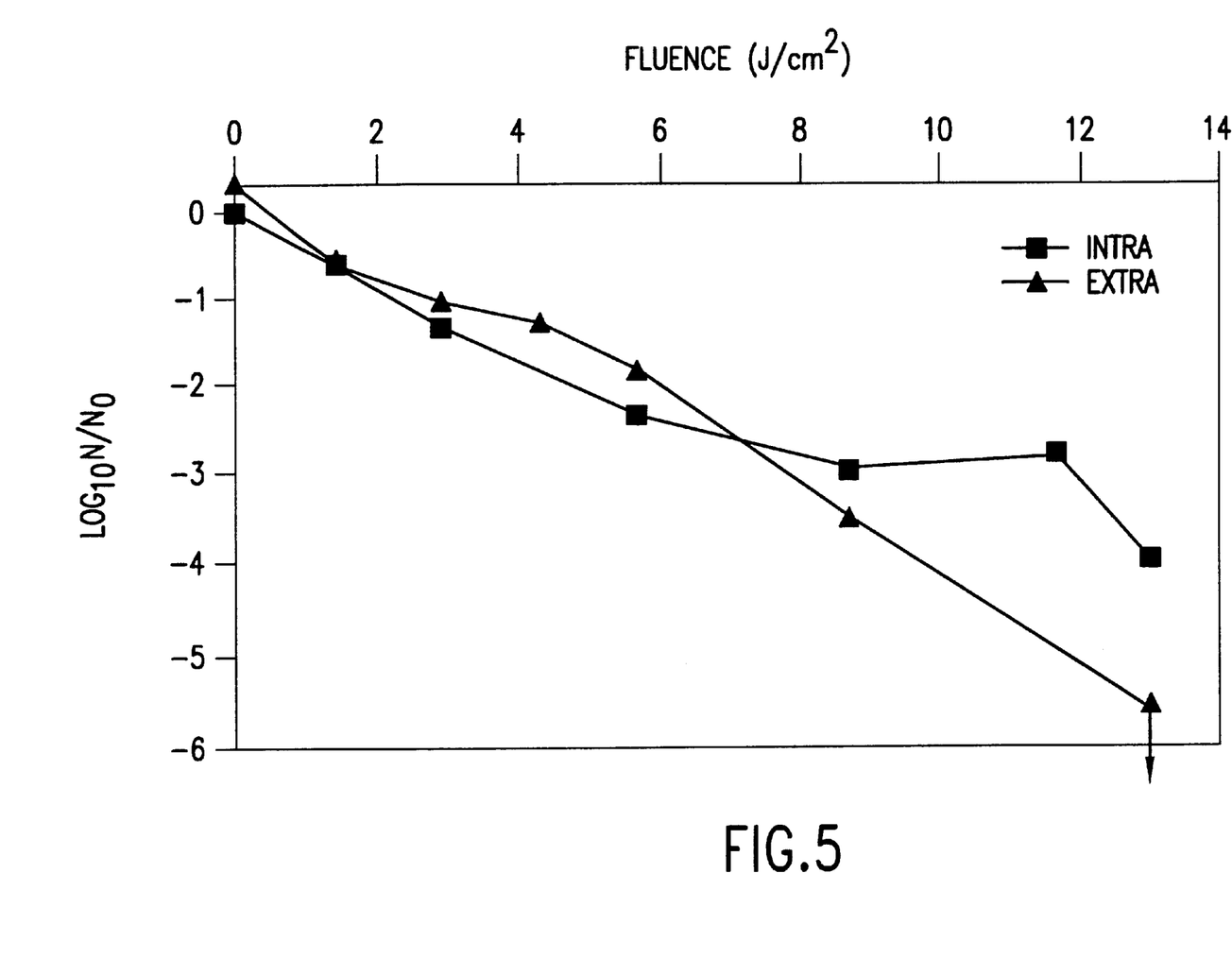
FIG. 5. VSV Photoinactivation in Red Cell Suspension by 4-91. Data from Example 1 are graphed here and show the effects of light fluence on the photoinactivation of intracellular and extracellular vesicular stomatitis virus in plasma containing red cells (30% hematocrit) suspended in ARC-8 using 4 μM of 4-91.

Plasma containing red cells (30% hematocrit) was suspended in ARC-8 and then treated with 4 $\mu$M 1,9-dimethyl methylene blue and 12.5 J/cm$^2$ light. The following results were obtained: >5.5 $\log_{10}$ inactivation of extracellular vesicular stomatitis virus (VSV) (FIG. 5); 4 $\log_{10}$ inactivation of intracellular VSV (FIG. 5); >7 $\log_{10}$ inactivation of the non-enveloped single stranded RNA bacteriophage R17 (FIG. 1); and 6.9 $\log_{10}$ inactivation of the enveloped, double stranded RNA bacteriophage Φ6 (FIG. 2).

Figure 2:
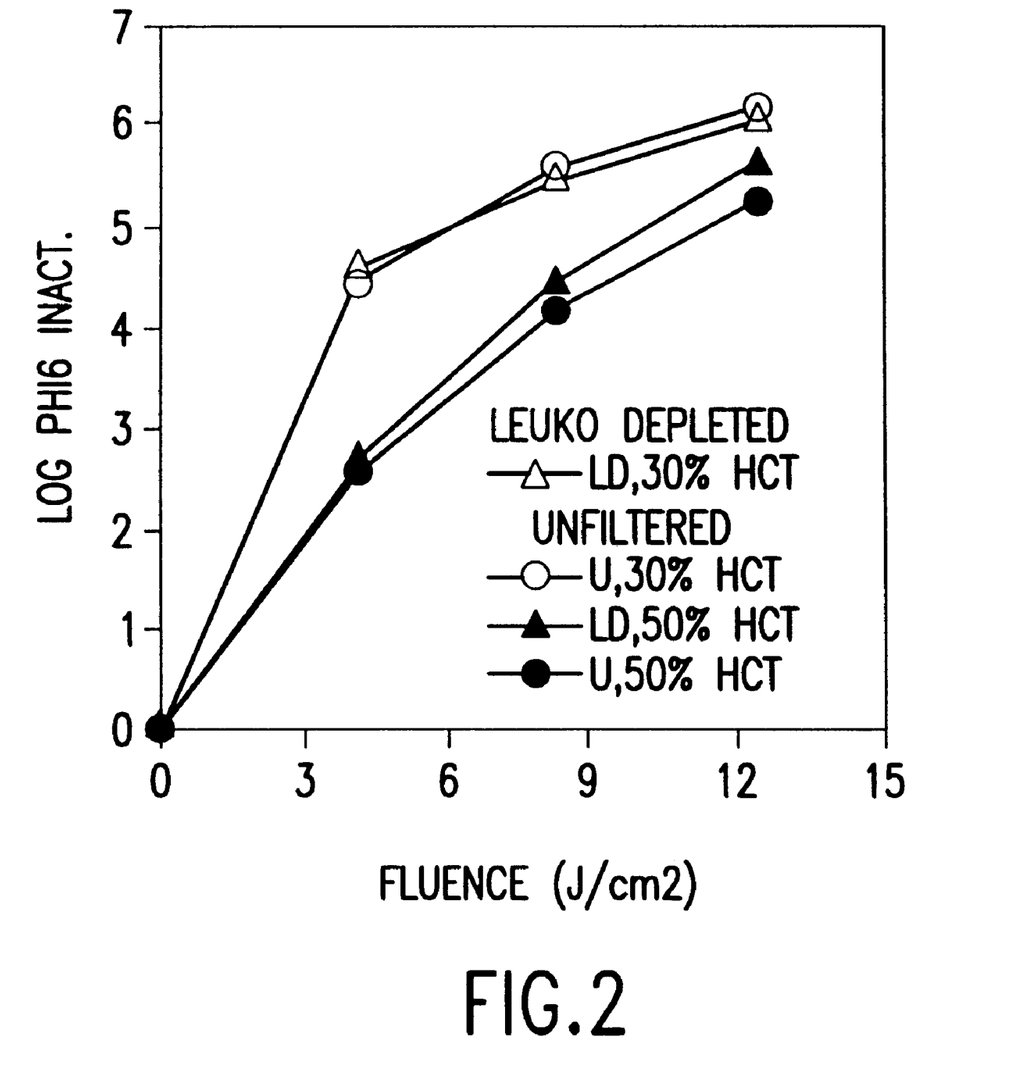
FIG. 2. Effect of Hematocrit and Leukoreduction on Φ6 Inactivation by Compound 4-91. Data from Example 1 are graphed here and show the effects of light fluence, hematocrit levels and leukoreduction on the photoinactivation of the enveloped, double-stranded RNA bacteriophage Φ6 in plasma containing red cells suspended in ARC-8 using 4 μM of compound 4-91.

Additional experiments with bacteriophage Φ6 under identical conditions achieved similar levels of viral inactivation in 50% hematocrit suspensions (FIG. 2).

Phototreatment of 30% hematocrit red cell suspensions (ARC-8) under virucidal conditions (4 $\mu$M of 1,9-dimethyl methylene blue and 12.5 J/cm$^2$ light) resulted in no detectable binding of IgG to phototreated red cells.

Figure 3:
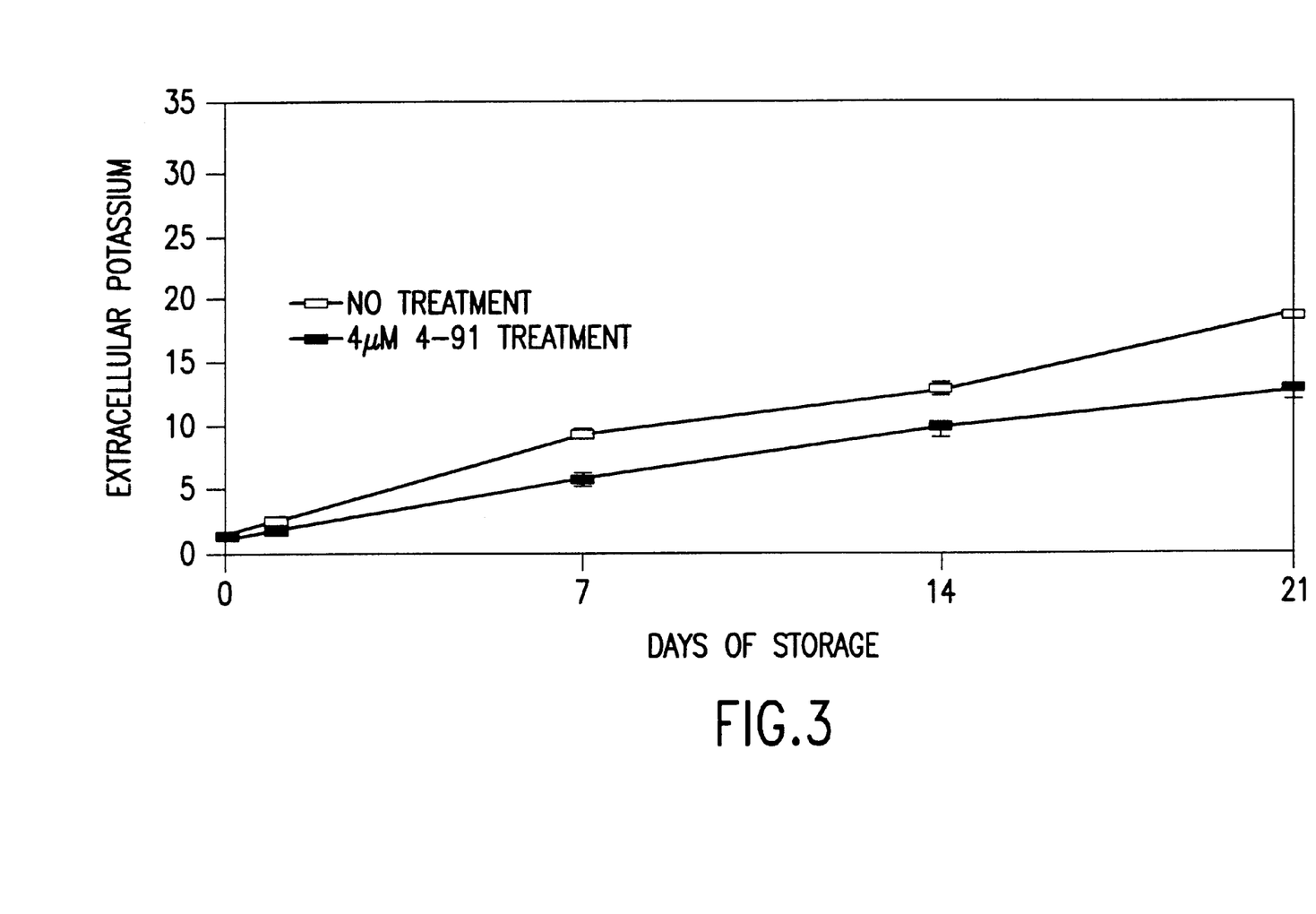
FIG. 3. Potassium Leakage During Storage. Data from Example 1 are graphed here and show that 4-91 treated red cells released potassium at roughly twice the rate of untreated red cells. This rate is similar to that observed with red cells that have been irradiated with 2500 rads of gamma (γ) radiation to prevent graft-versus-host disease. These data show that 4-91 treated red cells released roughly half of their intracellular potassium to the supernatant in 17 days; this compares with only 2–4 days for methylene blue treated cells.

As shown in FIG. 3, the rate of potassium release from cells treated with 1,9-dimethyl methylene blue was roughly twice that of untreated control cells and is similar to the rate observed with in red cells that have been irradiated with gamma ($\gamma$) rays (2500 rads) to prevent graft-versus-host disease. For cells treated with 1,9-dimethyl methylene blue, roughly ½ of intracellular potassium is released to the supernatant in 17 days; this compares with 2–4 days following treatment with methylene blue.

Figure 6:
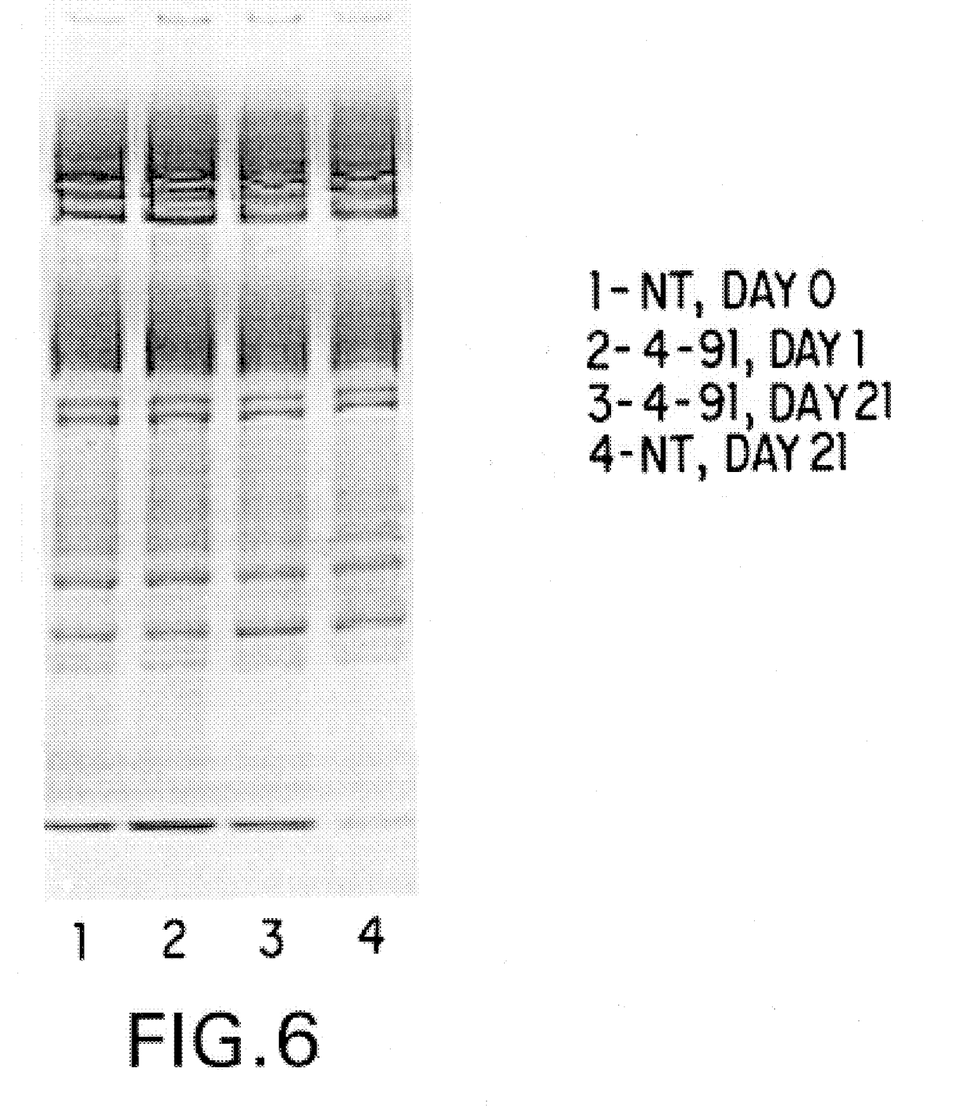
FIG. 6. Ghost Erythrocyte Membrane Proteins. Data from Example 1 are graphed here and show that phototreatment of 30% hematocrit red cell suspensions with compound 4-91 under virucidal conditions produced no detectable change in the banding pattern of red cell membrane proteins on SDS-PAGE when compared to untreated controls.

As shown in FIG. 6, no change was observed in the banding pattern on SDS-PAGE of red cell membrane proteins isolated from red cells treated with 1,9-dimethyl methylene blue as compared to the banding pattern of proteins isolated from control cells.

Figure 4:
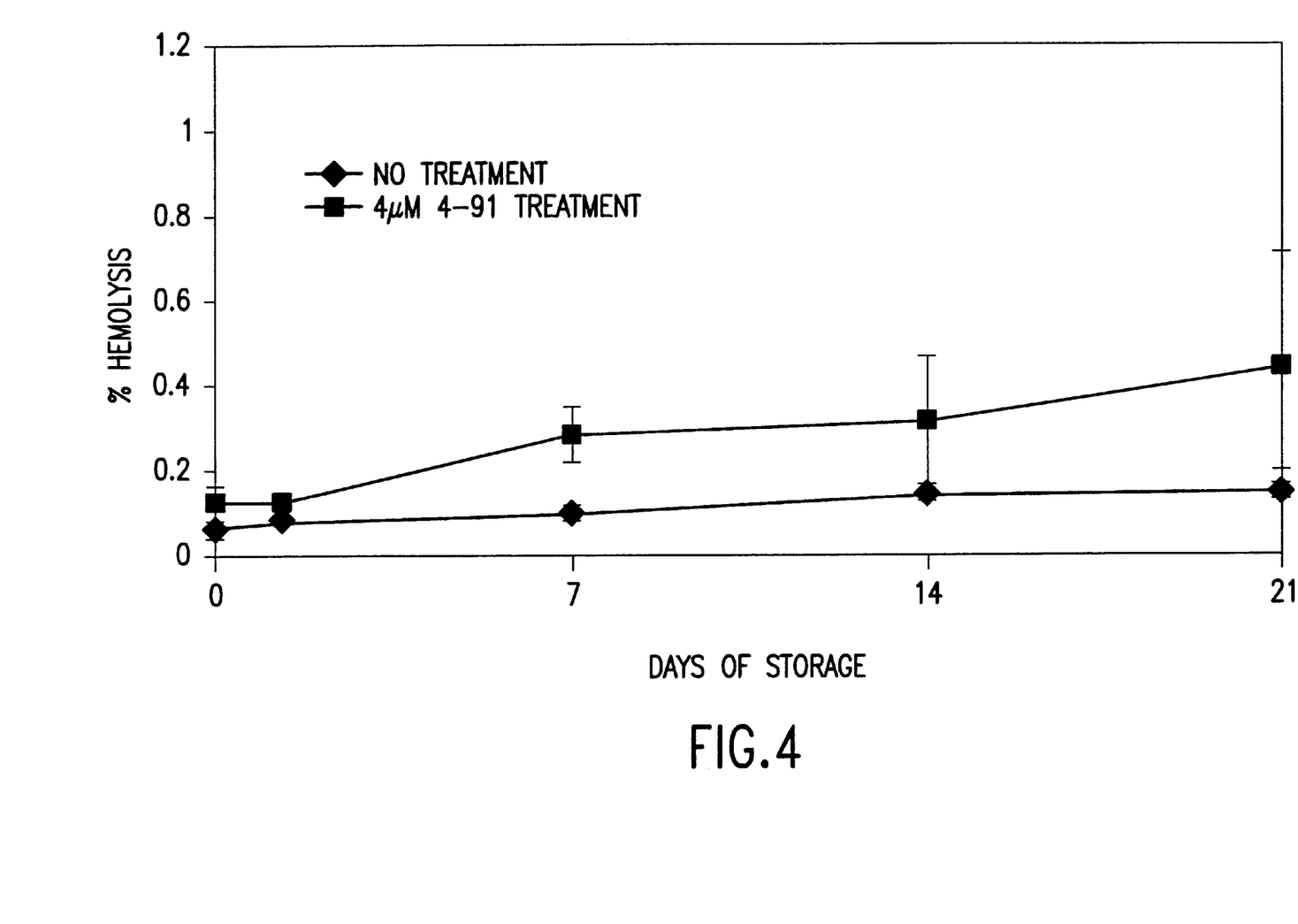
FIG. 4. Red Cell Hemolysis During Storage. Data from Example 1 are graphed here and show that 4-91 treated red cells exhibited 0.4% hemolysis after 21 days of storage at 1–6° C.

As shown in FIG. 4, samples treated with 1,9-dimethyl methylene blue exhibited 0.4% hemolysis after 21 days storage at 1–6° C.

EXAMPLE 2

A buffy coat was adjusted to 30% hematocrit with ARC-8, a red cell storage solution, and divided into two parts. One part was treated with 4 $\mu$M 1,9-dimethyl methylene blue and 13.1 J/cm$^2$ light for 45 minutes, while the other part was not treated.

Equivalent numbers of lymphocytes were isolated by gradient centrifugation from the control and phototreated samples, and subsequently cultured at 37° C. and 5% CO$_2$/air in RPMI 1640 containing 10% autologous plasma.

A non-radioactive assay based on the enzymatic reduction of MTS (3-[4,5-dimethylthiazol-2-yl]-5-(3-carboxymethyl phenyl)-2-(4-sulfophenyl)-2H-tetrazolium) was used to evaluate lymphocyte viability in the samples. Using an electro coupling reagent (phenazine ethosulfate), MTS is cleaved to a colored compound (formazan) by a mitrochondrial respiratory enzyme (succinate tetrazolium reductase) in the presence of NADH. The colored product is detected spectrophotometrically and is linearly proportional to the lymphocyte cell number as well as the reductive power of the cell.

Figure 7:
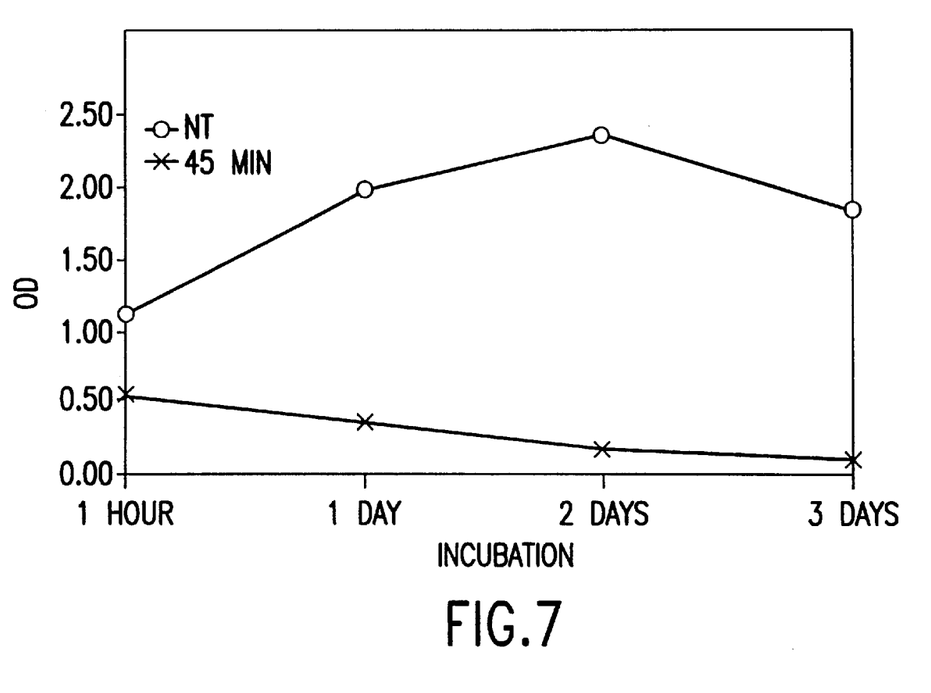
FIG. 7. Lymphocyte Proliferation During Incubation After Phototreatment. Data from Example 2 are graphed here and show that phototreatment of 30% hematocrit buffy coat with compound 4-91 prevented lymphocyte proliferation during subsequent incubation.

Analysis of the control sample during incubation showed that the control cells produced increasing amounts of formazen for two days, following which formazen production declined due to the acidity of the medium resulting from high cell densities (as shown in FIG. 7).

Analysis of the phototreated sample during incubation showed that, from the outset, the phototreated cells exhibited a markedly reduced capability to produce formazen when compared to the control cells. Formazen production by the phototreated cells continued to decline throughout incubation, eventually approaching background levels (as shown in FIG. 7).

These results strongly suggest that lymphocyte proliferation is prevented by phototreatment.

What is claimed is:

1. A method for reducing the level of active pathogenic contaminants in whole blood or blood components comprising the steps of:

(a) adding to said whole blood or blood components at least one amphiphilic phenothiazin-5-ium dye in an amount effective to reduce the level of active pathogenic contaminants, wherein said amphiphilic phenothiazin-5-ium dye has the formula wherein
each of $R_1$, $R_1'$, $R_2$, and $R_2'$ is independently selected from the group consisting of a methyl group, an ethyl group, a propyl group, an alkenyl group, an alkynyl group, nitrile, an aralkyl group, a hydroxy group, an alkoxy group, an amine group, and a hydrogen atom,
each of $R_3$, $R_3'$, $R_4$, $R_4'$, $R_5$ and $R_5'$ is independently selected from the group consisting of an alkyl group, an alkenyl group, an alkynyl group, a nitrile, an azide, an aryl group, an aralkyl group, a heteroaryl group, an alkoxy group, an aryloxy group, an amine group, and a hydrogen atom, or
any two of $R_1$, $R_1'$, $R_2$, $R_2'$, $R_3$, $R_3'$, $R_4$, $R_4'$, $R_5$ and $R_5'$ together form an aryl or heteroaryl ring;
Y is selected from the group consisting of S, Se and Te; and
X is a counter-ion; with the provisos:
(i) that if each of $R_1$, $R^{1'}$, $R_2$ and $R_2'$ is independently a hydrogen atom or an alkyl group, then at least one of $R_3$, $R_3'$, $R_4$, $R_4'$, $R_5$ and $R_5'$ is other than a hydrogen atom,
(ii) that if one of $R_4$ and $R_4'$ is an alkyl group, then at least one other of $R_3$, $R_3'$, $R_4$, $R_4'$, $R_5$ and $R_5'$ is other than a hydrogen atom,
(iii) that if any two of $R_3$, $R_3'$, $R_4$, $R_4'$, $R_5$ and $R_5'$ together form an aryl or heteroaryl ring, each of $R_1$, $R_1'$, $R_2$, $R_2'$ is other than a hydrogen atom; and
(b) irradiating said whole blood or blood components with light of an appropriate intensity and wavelength for a time sufficient to reduce the level of said active pathogenic contaminants in said whole blood or blood components.

2. The method of claim 1, wherein each of $R_1$, $R_1'$, $R_2$ and $R_2'$ is independently a methyl group, an ethyl group or a hydrogen atom.

3. The method of claim 1, wherein each of $R_3$ and $R_3'$ is a methyl group.

4. The method of claim 1, wherein each of $R_1$, $R_1'$, $R_2$ and $R_2'$ is a methyl group.

5. The method of claim 1, wherein said appropriate wavelength is between about 500 nm and about 800 nm.

6. The method of claim 1, wherein said pathogenic contaminants are selected from the group consisting of viruses, bacteria, parasites and leukocytes.

7. The method of claim 6, wherein said viruses are selected from the group consisting of intracellular viruses and extracellular viruses.

8. The method of claim 6, wherein said viruses are enveloped viruses.

9. The method of claim 8, wherein said enveloped viruses include at least one virus selected from the group consisting of RNA viruses and DNA viruses.

10. The method of claim 9, wherein said enveloped viruses include one or more viruses selected from the group consisting of human immunodeficiency virus, cytomegalovirus, herpes virus, hepatitis B virus, hepatitis C virus, Vesicular Stomatitis virus, Sindbis virus, and pox virus.

11. The method of claim 6, wherein said bacteria include members of the genus Streptococcus or the genus Escherichia.

12. The method of claim 6, wherein said parasites include members of the genus Trypanosoma.

13. The method of claim 1, further comprising the step of leukodepleting said whole blood or blood components prior to step (a).

14. The method of claim 1, wherein said effective amount is an amount sufficient to provide a concentration of said dye in said whole blood or blood components of between about 0.2 $\mu$M and about 50 $\mu$M.

15. The method of claim 1, wherein said effective amount is an amount sufficient to provide a concentration of said dye in said whole blood or blood components of between about 1 $\mu$M and about 25 $\mu$M.

16. The method of claim 1, wherein said amphiphilic phenothiazin-5-ium dye is 1,9-dimethyl methylene blue.

17. The method of claim 1, wherein each of $R_3$ and $R_3'$ is independently an alkyl group.

18. The method of claim 1, wherein each of $R_1$, $R_1'$, $R_2$, and $R_2'$, is independently a methyl group, an ethyl group, a propyl group, a lower alkynyl group, or a hydrogen atom, and each of $R_3$, $R_3'$, $R_4$, $R_4'$, $R_5$ and $R_5'$ is independently a lower alkynyl group, a lower alkynyl group, or a hydrogen atom.

19. The method of claim 18, wherein said lower alkyl group is a methyl group or an ethyl group.

* * * * *

UNITED STATES PATENT AND TRADEMARK OFFICE
CERTIFICATE OF CORRECTION

PATENT NO. : 6,030,767

DATED : February 29, 2000

INVENTORS : Wagner *et al.*

It is certified that an error appears in the above-identified patent and that said Letters Patent is hereby corrected as shown below.

In column 13, line 20, claim 1, please delete "nitrile", and insert therein --a nitrile--.

In column 13, line 32, claim 1, please delete "R'", and insert therein --$R_1'$--.

In column 14, lines 47-48, claim 18, please delete "independently a lower alkynyl group", and insert therein --independently a lower alkyl group--.

Signed and Sealed this

Twentieth Day of March, 2001

Attest:

NICHOLAS P. GODICI

*Attesting Officer*  *Acting Director of the United States Patent and Trademark Office*